(12) United States Patent
Stigall et al.

(10) Patent No.: US 11,883,235 B2
(45) Date of Patent: Jan. 30, 2024

(54) PHASED ARRAY IMAGING AND THERAPY INTRALUMINAL ULTRASOUND DEVICE

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US); Robert Emmett Kearney, San Diego, CA (US)

(73) Assignee: PHILIPS IMAGE GUIDED THERAPY CORPORATION, San Diego, CA (US)

(\*) Notice: Subject to any disclaimer, the term of this patent is extended or adjusted under 35 U.S.C. 154(b) by 399 days.

(21) Appl. No.: 16/103,802

(22) Filed: Aug. 14, 2018

(65) Prior Publication Data
US 2019/0053785 A1    Feb. 21, 2019

Related U.S. Application Data

(60) Provisional application No. 62/545,951, filed on Aug. 15, 2017.

(51) Int. Cl.
| | |
|---|---|
| *A61B 8/12* | (2006.01) |
| *A61N 7/00* | (2006.01) |
| *A61B 8/00* | (2006.01) |

(52) U.S. Cl.
CPC .......... *A61B 8/445* (2013.01); *A61B 8/12* (2013.01); *A61B 8/4494* (2013.01); *A61N 7/00* (2013.01); *A61B 8/4488* (2013.01); *A61B 8/54* (2013.01); *A61N 2007/0043* (2013.01)

(58) Field of Classification Search
None
See application file for complete search history.

(56) References Cited

U.S. PATENT DOCUMENTS

| | | | |
|---|---|---|---|
| 5,558,092 A * | 9/1996 | Unger | A61B 8/0833 600/439 |
| 6,049,958 A * | 4/2000 | Eberle | A61B 1/0011 29/25.35 |
| 6,200,268 B1 | 3/2001 | Vince | |
| 6,381,350 B1 | 4/2002 | Klingensmith | |
| 6,641,540 B2 | 11/2003 | Fleischman | |
| 6,776,763 B2 | 8/2004 | Kobayashi | |

(Continued)

OTHER PUBLICATIONS

Shung "Diagnostic Ultrasound: Imaging and Blood Flow Measurements" 2006 (Year: 2006).*

(Continued)

*Primary Examiner* — Colin T. Sakamoto

(57) ABSTRACT

Intraluminal ultrasound devices, systems and methods are provided. In one embodiment, an intravascular ultrasound device includes a flexible elongate member configured to be positioned within a body lumen of a patient, the flexible elongate member including a distal portion and a longitudinal axis; a first ultrasound transducer array configured to obtain ultrasound imaging data of the body lumen; and a second ultrasound transducer array configured to apply an ultrasound therapy within the body lumen. Both the first and second ultrasound transducer arrays are disposed at the distal portion of the flexible elongate member and circumferentially positioned around the longitudinal axis of the flexible elongate member.

12 Claims, 11 Drawing Sheets

(56) References Cited

U.S. PATENT DOCUMENTS

| | | |
|---|---|---|
| 7,074,188 B2 | 7/2006 | Nair |
| 7,175,597 B2 | 2/2007 | Vince |
| 7,215,802 B2 | 5/2007 | Klingensmith |
| 7,226,417 B1 | 6/2007 | Eberle |
| 7,359,554 B2 | 4/2008 | Klingensmith |
| 7,463,759 B2 | 12/2008 | Klingensmith |
| 2006/0036167 A1* | 2/2006 | Shina ............. A61B 6/481 600/433 |
| 2006/0206028 A1* | 9/2006 | Lee ............. A61B 17/3203 600/471 |
| 2007/0066902 A1* | 3/2007 | Wilser ............. B06B 1/0292 600/459 |
| 2007/0073135 A1* | 3/2007 | Lee ............. A61N 7/022 600/407 |
| 2009/0264759 A1* | 10/2009 | Byrd ............. A61M 25/0136 600/445 |
| 2012/0265227 A1* | 10/2012 | Sverdlik ............. A61M 25/10 606/169 |
| 2014/0005521 A1* | 1/2014 | Kohler ............. A61B 6/4057 601/3 |
| 2014/0187960 A1* | 7/2014 | Corl ............. B06B 1/0207 29/25.01 |
| 2014/0330124 A1* | 11/2014 | Carol ............. A61N 7/022 601/2 |
| 2016/0008636 A1* | 1/2016 | Warnking ............. A61B 8/483 600/411 |

OTHER PUBLICATIONS

Phased Array Imaging and Therapy Intraluminal Ultrasound Drive, U.S. Appl. No. 62/545,951, filed Aug. 15, 2017.

Intracardiac Therapeutic and Diagnostic Ultrasound Device, U.S. Appl. No. 62/545,927, filed Aug. 15, 2017.

Frequency-Tunable Intraluminal Ultrasound Device, U.S. Appl. No. 62/545,954, filed Aug. 15, 2017.

Intraluminal Rotational Ultrasound for Diagnostic Imaging and Therapy, U.S. Appl. No. 62/545,888, filed Aug. 15, 2017.

Pre-Doped Solid Substrate for Intravascular Devices, U.S. Appl. No. 61/985,220, filed Apr. 28, 2014.

\* cited by examiner

PHASED ARRAY IMAGING AND THERAPY INTRALUMINAL ULTRASOUND DEVICE

TECHNICAL FIELD

The present disclosure relates generally to intraluminal ultrasound device and, in particular, intraluminal ultrasound device with both imaging and therapeutic functions. For example, an intraluminal ultrasound device can include a first ultrasound transducer array for imaging and a second ultrasound transducer array for applying an ultrasound therapy.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy with frequencies higher than 10 MHz to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Ultrasound has been used in some drug delivery and therapeutic applications. Conventionally, due to the different in operation frequencies between the two, an ultrasound imaging device and an ultrasound therapeutic device are separate and distinct. In the case of intravascular imaging and therapy, both the ultrasound imaging device and the ultrasound therapeutic device have to be inserted into and withdrawn from the patient's blood vessel at least once during a procedure workflow. To evaluate the effectiveness of an ultrasound therapy, the intravascular therapy device has to be withdrawn from the patient's blood vessel, and the imaging device has to be re-inserted in to the blood vessel. This multiplicity of insertion and withdrawal of ultrasound devices not only is time-consuming but also can increase chances of clinical complications, such as blood vessel damage.

SUMMARY

Embodiments of the present disclosure provide an intraluminal ultrasound device that includes two ultrasound transducer arrays circumferentially positioned around a longitudinal axis of a flexible elongate member. One of the ultrasound transducer arrays is configured to operate at a high frequency range to obtain ultrasound imaging data of a body lumen of a patient and the other ultrasound transducer array is configured to operate at a low frequency range to apply ultrasound therapy to the body lumen. The two ultrasound transducer arrays can be positioned adjacently around the same tubular member or apart around two different tubular members. In the latter case, the two tubular members are coupled together by a flexible joint. The two ultrasound transducers according to the present disclosure can be control by the same control circuit or separately by two control circuits.

In one embodiment, an intravascular ultrasound device includes a flexible elongate member configured to be positioned within a body lumen of a patient, the flexible elongate member including a distal portion and a longitudinal axis; a first ultrasound transducer array configured to obtain ultrasound imaging data of the body lumen; and a second ultrasound transducer array configured to apply an ultrasound therapy within the body lumen. Both the first and second ultrasound transducer arrays are disposed at the distal portion of the flexible elongate member and circumferentially positioned around the longitudinal axis of the flexible elongate member.

In some embodiments, the first ultrasound transducer array and the second ultrasound transducer array of the intravascular ultrasound device are disposed around a tubular member. In some embodiments, wherein the first ultrasound transducer array and the second ultrasound transducer array of the intravascular device are coupled to a control circuit configured to selectively activate a whole or part of the first ultrasound transducer array and the second ultrasound transducer array. In some other embodiments, the first ultrasound transducer array is disposed around a first tubular member and the second ultrasound transducer array is disposed around a second tubular member. In these embodiments, the first tubular member is coupled to the second tubular member via a flexible member. In some instances, the first ultrasound transducer array is coupled to a first control circuit configured to control the first ultrasound transducer array and the second ultrasound transducer array is coupled to a second control circuit configured to control the second ultrasound transducer array. In some implementations, the first ultrasound transducer array is operable at a first frequency range having a first median, wherein the second ultrasound transducer array is operable at a second frequency range having a second median lower than the first median. In some instances, the first frequency range and the second frequency range do not overlap. In some embodiments, the first frequency range comprises frequencies between 10 MHz and 70 MHz and the second frequency range comprises frequencies between 1 KHz and 20 MHz. In some instances, the first ultrasound transducer array comprises a first plurality of ultrasound transducers mounted on a first flexible substrate rolled around the longitudinal axis of the flexible elongate member, and the second ultrasound transducer array comprises a second plurality of ultrasound transducers mounted on a second flexible substrate rolled around the longitudinal axis of the flexible elongate member.

In another embodiment, a method for treating a target site within a body lumen of a patient is provided. The method includes obtaining ultrasound imaging data of the body lumen with a first ultrasound transducer array disposed at a distal portion of a flexible elongate member of an intraluminal ultrasound device; and applying the ultrasound therapy to the target site within the body lumen with the second ultrasound transducer array. The intraluminal ultrasound device includes the flexible elongate member configured to be positioned within the body lumen of the patient, the flexible elongate member including the distal portion and a longitudinal axis, the first ultrasound transducer array disposed at the distal portion of the flexible elongate member and circumferentially positioned around the longitudinal axis of the flexible elongate member, the first ultrasound transducer array configured to obtain ultrasound imaging data of the body lumen, and a second ultrasound transducer array disposed at the distal portion of the flexible elongate member and circumferentially positioned around the longitudinal axis of the flexible elongate member, the second ultrasound transducer array configured to apply an ultrasound therapy to the target site within the body lumen.

In some embodiments, the intraluminal ultrasound device is in communication with an ultrasound processing system and the method for treating a target site within a body lumen of a patient further includes: after obtaining ultrasound imaging data of the body lumen, determining by the ultrasound processing system, a diameter of the body lumen and a level of calcification of the target site based on the obtained ultrasound imaging data; and determining a first set of ultrasound parameters for the second ultrasound transducer array based on the determined diameter of the body lumen and the level of calcification of the target site. In some instances, the second ultrasound transducer array operates under the first set of ultrasound parameters when applying the ultrasound therapy to the target site with ultrasound transducer array. In some implementations, the method for treating a target site within a body lumen of a patient further includes: after applying the ultrasound therapy to the target site, obtaining ultrasound imaging data of the body lumen using the first ultrasound transducer array; determining, by using the ultrasound processing system, an updated diameter of the body lumen and an updated level of calcification of the target site based on the obtained ultrasound imaging data; determining a second set of ultrasound parameters for the second ultrasound transducer array based on the updated diameter of the body lumen and the updated level of calcification of the target site; and applying the ultrasound therapy to the target site within the body lumen with the second ultrasound transducer array operating under the second set of ultrasound parameters. In some instances, the first set of ultrasound parameters comprises a frequency, a pulse amplitude, and a pulse length. In some instances, the second set of ultrasound parameters comprises a frequency, a pulse amplitude, and a pulse length. In some embodiments, the method for treating a target site within a body lumen of a patient further includes treating the target site with a treatment component, wherein the treatment component comprises a balloon, a stent, a needle, an ablation electrode, a mechanical cutting component, a rotational cutting device, an aspiration device, a targeted drug delivery device, a drug coated balloon, or a drug coated stent.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
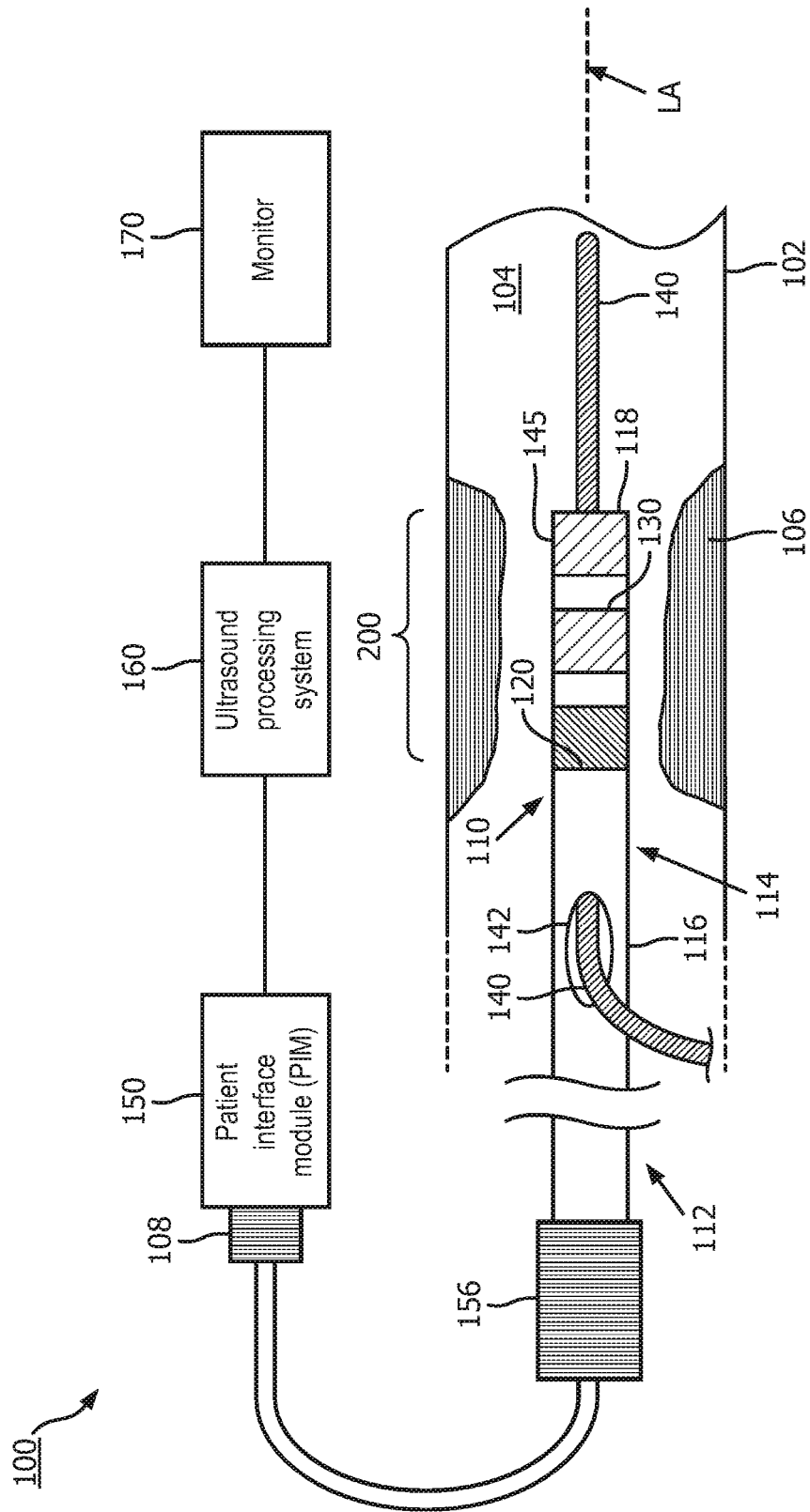
FIG. 1 is a diagrammatic schematic view of an ultrasound system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The system 100 can include an ultrasound device 110, a patient interface module (PIM) 150, an ultrasound processing system 160 (sometimes referred to as a computer system), and/or a monitor 170. The ultrasound device 110 is structurally arranged (e.g., sized and/or shaped) to be positioned within anatomy 102 of a patient. The ultrasound device 110 obtains ultrasound imaging data from within the anatomy 102 and applies ultrasound therapy to the anatomy 102. The ultrasound processing system 160 can control the acquisition of ultrasound imaging data and/or the application of ultrasound therapy, and generates an image of the anatomy 102 (using the ultrasound imaging data received via the PIM 150) that is displayed on the monitor 170.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 (or body lumen) of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr and approximately 15 Fr, including values such as 3.5 Fr, 5 Fr, 7 Fr, 8.2 Fr, 9 Fr, and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the ultrasound device 110. In the illustrated embodiment, the ultrasound device 110 is a catheter and includes a lumen at the distal portion 114 of the flexible elongate member 116. A guide wire 140 extends through the lumen of the ultrasound device 110 between an exit/entry port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the exit/entry port 142 is positioned proximally of ultrasound components 120, 130, and 145 of the ultrasound device 110. In some embodiments, the exit/entry port 142, the exit/entry port at the distal end 118, and/or the lumen of the ultrasound device 110 is positioned distally of the ultrasound components 120, 130, and 145. In some embodiments, the ultrasound device 110 is not used with a guide wire, and the exit/entry port 142 can be omitted from the ultrasound device 110. For ease of reference, the assembly that includes the ultrasound components 120, 130, and 145 is referred to as the transducer assembly 200. The ultrasound components 120, 130 and 145 can sometimes be structures other than ultrasound transducers or an ultrasound transducer arrays and therefore can also be referred to as ultrasound structures 120, 130 and 145.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device or an intraluminal ultrasound device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the ultrasound device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the ultrasound device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 includes ultrasound components 120 and 130 at the distal portion 114 of the flexible elongate member 116. The ultrasound components 120 and 130 are configured to emit ultrasonic energy into the anatomy 102 while the ultrasound device 110 is positioned within the lumen 104. In some embodiments, the two ultrasound components 120 and 130 are distinct. In other embodiments, the two ultrasound components 120 and 130 are the same ultrasound component or part of the same ultrasound component. One of the ultrasound components 120, 130 is configured for diagnostic use, while the other of the ultrasound components 120, 130 is configured for therapeutic use. For example, the ultrasound components 120, 130 can emit different frequencies of ultrasonic energy into the anatomy 102 depending on whether the ultrasonic energy is being used for diagnosis, such as imaging, and/or treatment.

In some embodiments, the ultrasound components 120 and/or 130 include ultrasound transducer(s). For example, the ultrasound components 120 and/or 130 can be configured to generate and emit ultrasound energy into the anatomy 102 in response to being activated by an electrical signal. In some embodiments, the ultrasound components 120 and/or 130 include a single ultrasound transducer. In some embodiments, the ultrasound components 120 and/or 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound components 120 and/or 130 can be any suitable configuration, such as phased array including a planar array, a curved array, a circumferential array, an annular array, etc. For example, the ultrasound component 120 and/or 130 can be a one-dimensional array or a two-dimensional array in some instances. In some instances, the ultrasound components 120 and/or 130 can be a rotational ultrasound device. The active area of the ultrasound components 120 and/or 130 can include one or more transducer materials and/or one or more segments of ultrasound elements (e.g., one or more rows, one or more columns, and/or one or more orientations) that can be uniformly or independently controlled and activated. The active area of the ultrasound components 120 and/or 130 can be patterned or structured in various basic or complex geometries. The ultrasound components 120 and/or 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the ultrasound components 120 and/or 130 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the ultrasound component 120 and/or 130.

The ultrasound transducer(s) of the ultrasound components 120 and/or 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the ultrasound component 120 is configured to obtain ultrasound imaging data associated with the anatomy 102, such as the occlusion 106. The ultrasound imaging data obtained by the ultrasound component 120 can be used by a medical professional to diagnose the patient, including evaluating the occlusion 106 of the anatomy 102. For imaging, the ultrasound component 120 can be configured to both emit ultrasonic energy into the lumen 104 and/or the anatomy 102, and to receive reflected ultrasound echoes representative of fluid and/or tissue of lumen 104 and/or the anatomy 102. As described herein, the ultrasound component 120 can be an ultrasound imaging element, such as an ultrasound transducer and/or an ultrasound transducer array. For example, the ultrasound component 120 generates and emits ultrasound energy into the anatomy 102 in response to transmission of an electrical signal to the ultrasound component 120. For imaging, the ultrasound component 120 generates and transmits an electrical signal representative of the received reflected ultrasound echoes from the anatomy 102 (e.g., to the PIM 150). In various embodiments, the ultrasound component 120 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

For diagnosis and/or imaging, the center frequency of the ultrasound component 120 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound component 120 is tunable. For imaging, in some instances, the ultrasound component 120 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound component 120.

In some embodiments, the ultrasound component 130 is configured to apply an ultrasound therapy to the anatomy 102, such as the occlusion 106. For example, the ultrasound component 130 emits sound waves that damage the structure of the occlusion 106. In that regard, the ultrasound device 110 and/or the ultrasound component 130 can be referenced as a lithotripsy device. The ultrasonic energy emitted by the ultrasound component 130 can create micro fractures in the calcium blockage of occlusion 106. For example, the ultrasound component 130 can deliver ultrasonic energy in a targeted manner to cause cavitation (e.g., wave force cavitation, thermal cavitation, etc.) of the occlusion 106. Delivery of ultrasound therapy by the ultrasound component 130 advantageously facilitates thrombus dilution and/or vessel preparation. For example, ultrasound therapy can be applied prior to delivery of a pharmacological agent to the anatomy 102. The pharmacological agent can be a thrombolytic agent, a fibrinolytic agent, plasmin, plasmid, tissue plasminogen activator, urokinase, streptokinase, collagenace, heparanoid, anti-thrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. Accordingly, the efficacy of the treatment and the health of the patient is improved.

In some embodiments, the ultrasound component 130 is an ultrasound element, such as an ultrasound transducer and/or ultrasound transducer array. For example, the ultrasound component 130 can be configured to generate and emit ultrasound energy into the anatomy 102 in response to transmission of an electrical signal to the ultrasound component 130. Unlike the ultrasound component 120, which is used of ultrasound imaging, the ultrasound component 130 need not be configured to receive ultrasonic echoes reflected the anatomy 102 and generate a representative electrical signal. For example, in some embodiments, the ultrasound component 130 is not an ultrasound element that generates ultrasound energy. Rather, the ultrasound components 130 can be an intermediate component that is configured to deliver ultrasound energy generated by an ultrasound component separate from the ultrasound device 110 (e.g., an external ultrasound transducer positioned outside of the body of the patient). For ultrasound therapy, the center frequency of the ultrasound component 130 can be between 1 kHz and 5 MHz, for example, including values such as 50 kHz, 500 kHz, 1 MHz, 3 MHz, and/or other suitable values both larger and smaller. In some embodiments, the frequency of the ultrasound component 130 is tunable. For example, the frequency of the emitted ultrasonic energy can be modified by the voltage of the applied electrical signal and/or the application of a biasing voltage to the ultrasound component 130.

In some embodiments, such as when the ultrasound components 120 and 130 both include ultrasound transducers, the ultrasound components 120 and 130 can be configured to generate and emit ultrasound energy, and to generate electrical signals representative of the received ultrasound echoes. One of the ultrasound components 120, 130 can be operated in diagnostic and/or imaging mode (generates and emits ultrasound energy, and generates electrical signals representative of the received ultrasound echoes), while the other of the ultrasound components 120, 130 is operated in therapeutic mode (generates and/or emits ultrasound energy).

In some embodiments, the ultrasound device 110 includes a treatment component 145. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to the anatomy 102, such as the occlusion 106. For example, the pharmacological agent can be delivered to the anatomy 102 by the treatment component 145 after the ultrasound therapy is applied to the anatomy 102 by the ultrasound component 130. In other embodiments, the ultrasound device 110 omits the treatment component 145.

In some embodiments, it is advantageous to position the components 120, 130, and/or 145 in one compact transducer assembly 200 because doing so can minimize the length of a relatively stiffer segment of the flexible elongate member 116. In some other embodiments, it is advantageous to position the component 120, 130, and/or 145 in separate transducer assemblies and couple them together with flexible members or flexible joints. This is so because the each of the transducer assembly carrying only one ultrasound component tends to be shorter in length. When coupled together by flexible members/joints, the transducer assemblies can be steerable through tortuous vasculature like cars of a train.

Generally, the ultrasound components 120, 130, and/or 145 are positioned at the distal portion of the flexible elongate member 116. The relative positioning of the ultrasound components 120, 130, and/or 145 can vary in different embodiments. In the illustrated embodiment, the diagnostic and/or imaging ultrasound component 120 is positioned proximally of the therapeutic ultrasound component 130. In other embodiments, the therapeutic ultrasound component 130 is positioned proximally of the diagnostic and/or imaging ultrasound component 120. In embodiments which include the treatment component 145, the treatment component 145 can be positioned proximally of the ultrasound components 120 and/or 130, distally of the ultrasound components 120 and/or 130, or between the ultrasound components 120 and/or 130.

The ultrasound components 120 and/or 130 can include one or more electrical conductors extending along the length from the flexible elongate member 116. The electrical conductor(s) are in communication with the ultrasound components 120, 130 at the distal portion 114, and an interface 156 at the proximal portion 112. The electrical conductors carry electrical signals between the ultrasound processing system 160 and the ultrasound components 120, 130. For example, activation and/or control signals can be transmitted from the ultrasound processing system 160 to the ultrasound components 120, 130 via the electrical conductors. Electrical signals representative of the reflected ultrasound echoes can be transmitted from the ultrasound components 120 and/or 130 to the ultrasound processing system 160 via the electrical conductors. In some embodiments, the same electrical conductors can be used for communication between the ultrasound processing system 160 and the ultrasound components 120 and/or 130. In other embodiments, different electrical conductors of the ultrasound device 110 can be used for communication between the ultrasound processing system 160 and the ultrasound component 120, and between the ultrasound processing system 160 and the ultrasound component 130.

The ultrasound device 110 includes an interface 156 at the proximal portion 112 of the flexible elongate member 116. In some embodiments, the interface 156 can include a handle. For example, handle can include one or more actuation mechanisms to control movement of the ultrasound device 110, such as deflection of the distal portion 114. In some embodiments, the interface 156 can include a telescoping mechanism that allows for pullback of the ultrasound device 110 through the lumen. In some embodiments, the interface 156 can include a rotation mechanism to rotate one or more components of the ultrasound device 110 (e.g., the flexible elongate member 116, the ultrasound components 120, 130). In some embodiments, the interface 156 includes a user interface component (e.g., one or more buttons, a switch, etc.) for a medical professional to selectively activate the ultrasound component 120 for imaging or the ultrasound component 130 for therapy. In other embodiments, a user interface component of the PIM 150, the ultrasound processing system 160 and/or the monitor 170 allows a medical profession to selectively activate the ultrasound component 120 for imaging or the ultrasound component 130 for therapy. A conduit including, e.g., electrical conductors, extends between the interface 156 and the connector 108. The connector 108 can be configured to mechanically and/or electrically couple the ultrasound device 110 to the PIM 150.

The ultrasound processing system 160, the PIM 150, and/or the ultrasound device 110 (e.g., the interface 156, the ultrasound components 120 and/or 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the ultrasound processing system 160. In examples of such embodiments, the PIM 150 performs amplification, filtering, and/or aggregating of the data. In an embodiment, the PIM 150 also supplies high- and low-voltage DC power to support operation of the ultrasound device 110 including circuitry associated with the ultrasound components 120 and/or 130. The PIM 150 can be an isolation device as, in various surgical settings, patient safety requirements mandate physical and electrical isolation of the patient from one or more high voltage components.

The ultrasound processing system 160 receives imaging data (e.g., electrical signals representative of the ultrasound echo data) from the ultrasound component 120 by way of the PIM 150. The ultrasound processing system 160 can include processing circuit, such as processor and/or memory. The ultrasound processing system 160 processes the data to reconstruct an image of the anatomy. The ultrasound processing system 160 outputs image data such that an image of the anatomy 102, such as a cross-sectional IVUS image of a vessel, is displayed on the monitor 170. The ultrasound processing system 160 and/or the monitor 170 can include one or more user interface elements (e.g., touchscreen, keyboard, mouse, virtual buttons on a graphical user interface, physical buttons, etc.) to allow a medical professional to control the ultrasound device 110, including one or more parameters of the ultrasound components 120, 130.

Figure 2A:
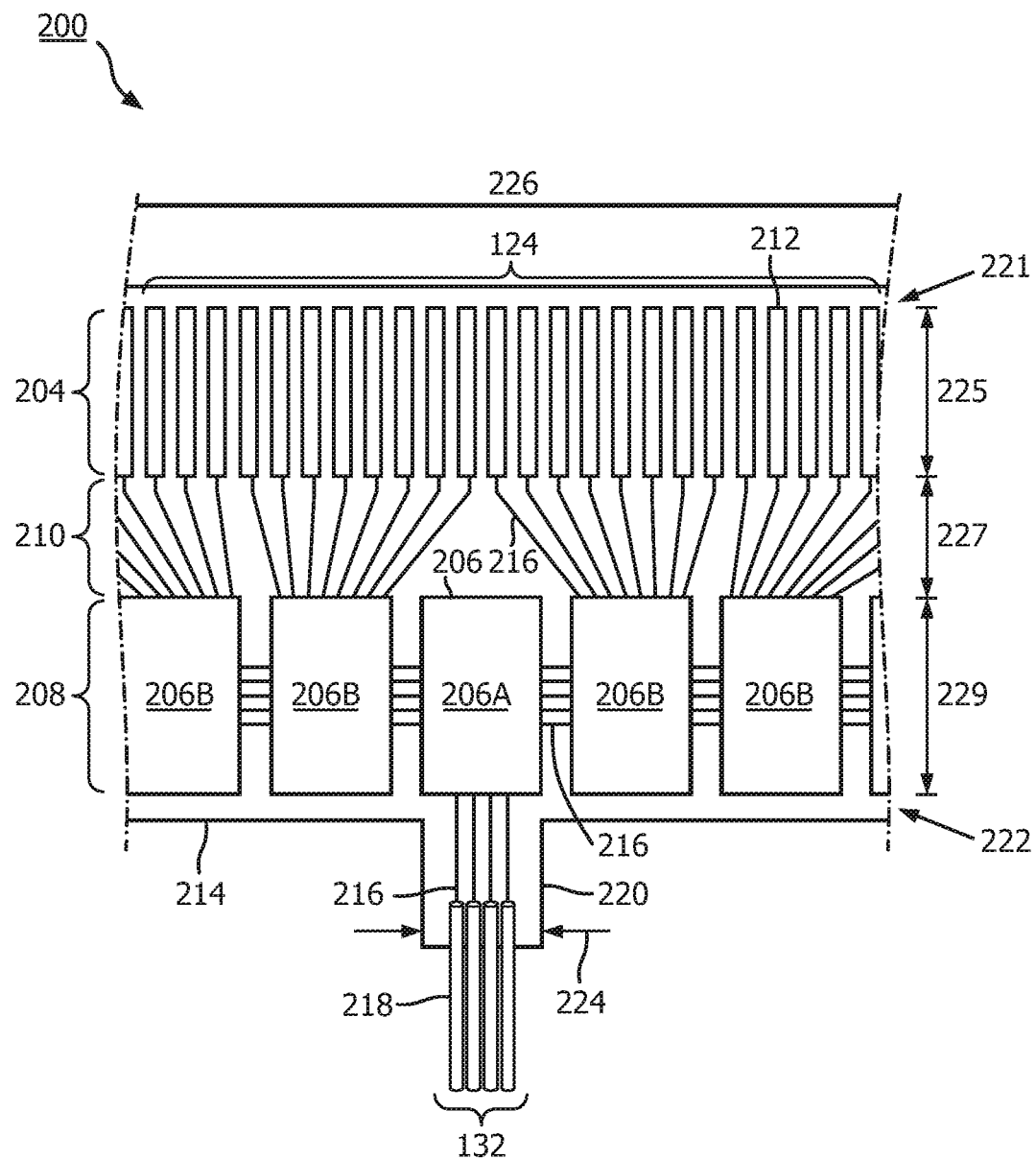
FIG. 2A is a diagrammatic top view of an transducer assembly with an ultrasound transducer array in a flat configuration, according to aspects of the present disclosure.

Referring now to FIG. 2A, shown therein is a top view of the transducer assembly 200 in a flat configuration according to an embodiment of the present disclosure. The transducer assembly 200 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flexible substrate 214 that is shown in a flat configuration in FIG. 2A. In some embodiments, the transducer control logic dies 206 in the control region 208 are in communication with the transducer array 124 via conductive traces 216 in the transition region 210. In these embodiments, the transducer control logic dies 206 controls and activates the transducer array 124 and can sometimes be referred to as a control circuit 206. In some implementations, the control circuit not only can activate the whole of the transducer array 124 but also a portion of the transducer array 124. In some embodiments, each of the ultrasound components 120 and 130 includes one transducer array 124. In some implementations where both the ultrasound device 110 includes both the ultrasound component 120 and the ultrasound component 130, the ultrasound device 110 would have two transducer arrays similar to transducer array 124 and two control circuits similar to the control circuit 206. Each of the two transducer arrays is controlled by one of the two control circuits.

Figure 3A:
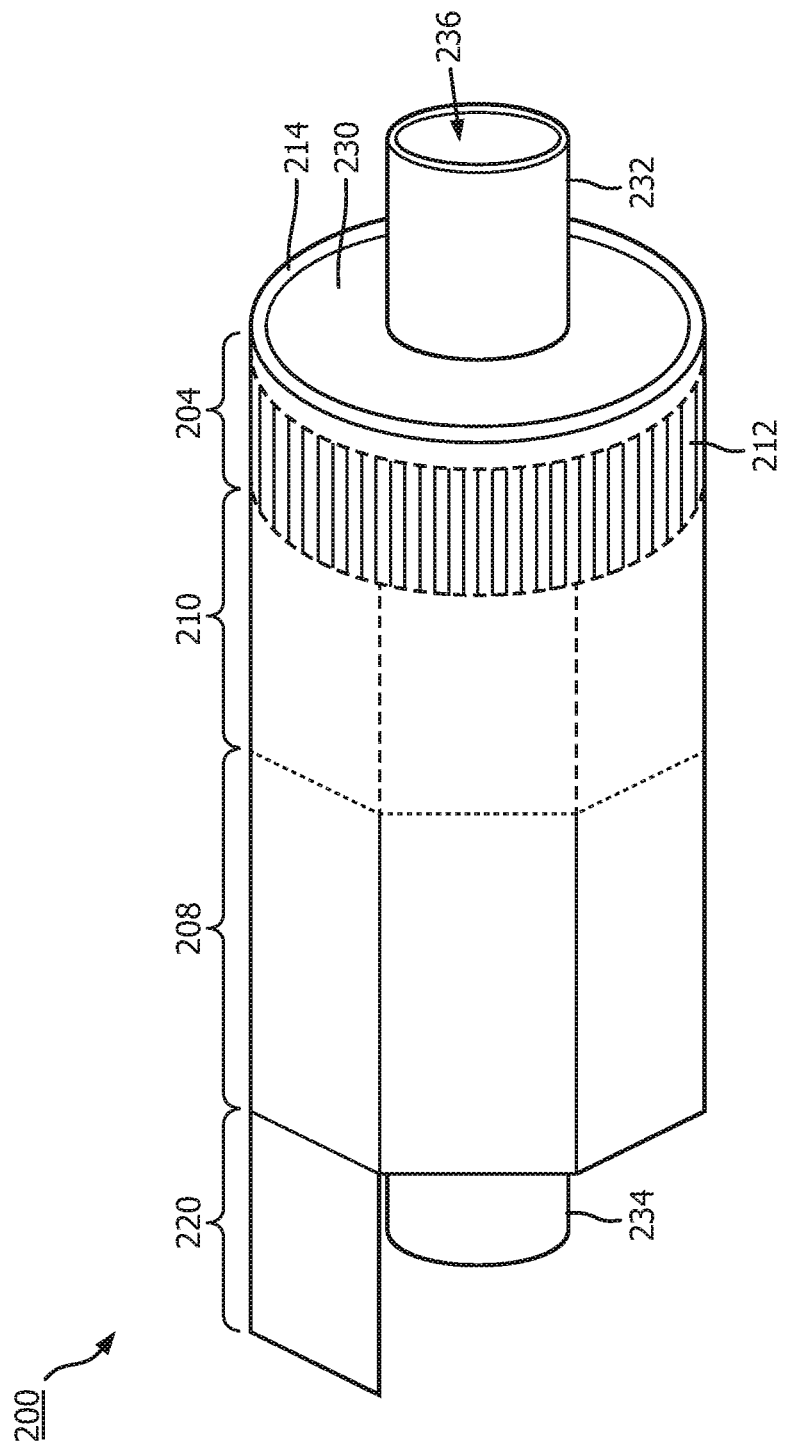
FIG. 3A is a diagrammatic perspective view of an transducer assembly with an ultrasound transducer array in a rolled configuration around a tubular member, according to aspects of the present disclosure.

FIG. 3A illustrates a rolled configuration of the flexible substrate 214 in FIG. 2A. The transducer array 124 is a non-limiting example of a medical sensor element and/or a medical sensor element array. The transducer control logic dies 206 is a non-limiting example of a control circuit 206. The transducer region 204 is disposed adjacent a distal portion 221 of the flexible substrate 214. The control region 208 is disposed adjacent the proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the transducer assembly 200 is described as including a flexible substrate, it is understood that the transducers and/or controllers may be arranged to form the transducer assembly 200 in other configurations, including those omitting a flexible substrate.

The transducer array 124 may include any number and type of ultrasound transducers 212, although for clarity only a limited number of ultrasound transducers are illustrated in FIG. 2A. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In some embodiments, one of the ultrasound components 120 and 130, each of which includes a transducer assembly 200, is configured to obtain ultrasound imaging data and the other is configured to apply an ultrasound therapy. For example, ultrasound component 130 is shown to be distal to the ultrasound component 120. In some implementations, ultrasound component 130 is configured to obtain ultrasound imaging data and ultrasound component 120 that is proximal to ultrasound component 130 is configured to apply the ultrasound therapy. A person skilled in the art, upon examination of the present disclosure, would appreciate that the ultrasound component 130 can be configured to apply the ultrasound therapy and the ultrasound component 120 proximal to the ultrasound component 130 can be configured to obtain ultrasound imaging data.

The transducer assembly 200 that is configured to obtain ultrasound imaging data may include various imaging control logic, which in the illustrated embodiment is divided into discrete control logic dies 206. In various examples directed to ultrasound components configured to obtain ultrasound imaging data, the imaging control logic of the transducer assembly 200 performs: decoding control signals sent by the PIM 150 across the electrical cable 132, driving one or more transducers 212 to emit an ultrasonic signal, selecting one or more transducers 212 to receive a reflected echo of the ultrasonic signal, amplifying a signal representing the received echo, and/or transmitting the signal to the PIM across the electrical cable 132. In the illustrated embodiment, an transducer assembly 200 having 64 ultrasound transducers 212 divides the control logic across nine control logic dies 206, of which five are shown in FIG. 2A. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

In some embodiments, the transducer array 124 that is configured to obtain ultrasound imaging data operates at frequencies between 10 MHz to 70 MHz. In some implementations, the transducer array 124 that is configured to obtain ultrasound imaging data operates at a frequency range falling between 10 MHz and 70 MHz. For ease of reference, this frequency range is referred to as diagnostic frequency range. In some instances, the diagnostic frequency range includes a median The transducer assembly 200 that is configured to apply an ultrasound therapy may include various therapy control logic, which in the illustrated embodiment is divided into discrete control logic dies 206. In various examples directed to ultrasound components 120/130 configured to apply an ultrasound therapy, the therapy control logic of the ultrasound component 120/130 performs: decoding control signals sent by the PIM 150 across the electrical cable 132, and driving one or more transducers 212 to emit an ultrasonic signal. In the illustrated embodiment, the transducer array 124 having 64 ultrasound transducers 212 divides the control logic across nine control logic dies 206, of which five are shown in FIG. 2A. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

In some embodiments, the transducer array that is configured to apply an ultrasound therapy operates at frequencies between 1 KHz to 20 MHz. In some implementations, the transducer array 124 that is configured to apply an ultrasound therapy operates at a frequency range falling between 1 KHz and 20 MHz, in some cases between 1 KHz and 5 MHz. For ease of reference, this frequency range is referred to as therapeutic frequency range. In some instances, the therapeutic frequency range includes a median. The median of the imaging frequency range is different from the median of the therapeutic frequency range. In some instances, the imaging frequency range overlaps with the therapeutic frequency range. In some other instances, the imaging frequency range does not overlap with the therapeutic frequency range.

The control logic dies are not necessarily homogenous. In some embodiments, a single controller is designated a master control logic die 206A and contains the communication interface for the electrical cable 132. Accordingly, the master control circuit may include control logic that decodes control signals received over the electrical cable 132, transmits control responses over the electrical cable 132, amplifies echo signals, and/or transmits the echo signals over the electrical cable 132. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2A, the flexible substrate 214 has a generally rectangular shape. As shown and described herein, the flexible substrate 214 is configured to be wrapped around a tubular member 230 (FIG. 3A) to form a cylindrical toroid in some instances. Therefore, the thickness of the film layer of the flexible substrate 214 is generally related to the degree of curvature in the final assembled ultrasound component 120/130. In some embodiments, the film layer is between 5 µm and 100 µm, with some particular embodiments being between 12.7 µm and 25.1 µm.

To electrically interconnect the control logic dies 206 and the transducers 212, in an embodiment, the flexible substrate 214 further includes conductive traces 216 formed on the film layer that carry signals between the control logic dies 206 and the transducers 212. In particular, the conductive traces 216 providing communication between the control logic dies 206 and the transducers 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of the electrical cable 132 when the conductors 218 of the electrical cable 132 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flexible substrate 214 may be further determined by the width of the conductor 218 to be coupled to the trace/pad.

The flexible substrate 214 can include a connection interface 220 in some embodiments. The connection interface 220 can be a location of the flexible substrate 214 where the conductors 218 of the electrical cable 132 are coupled to the flexible substrate 214. For example, the bare conductors of the electrical cable 132 are electrically coupled to the flexible substrate 214 at the connection interface 220. The connection interface 220 can be a tab extending from the main body of flexible substrate 214. In that regard, the main body of the flexible substrate 214 can refer collectively to the transducer region 204, controller region 208, and the transition region 210. In the illustrated embodiment, the connection interface 220 extends from the proximal portion 222 of the flexible substrate 214. In other embodiments, the connection interface 220 is positioned at other parts of the flexible substrate 214, such as the distal portion 221, or the flexible substrate 214 omits the connection interface 220. A value of a dimension of the tab or connection interface 220, such as a width 224, can be less than the value of a dimension of the main body of the flexible substrate 214, such as a width 226. In some embodiments, the substrate forming the connection interface 220 is made of the same material(s) and/or is similarly flexible as the flexible substrate 214. In other embodiments, the connection interface 220 is made of different materials and/or is comparatively more rigid than the flexible substrate 214. For example, the connection interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the tubular member 230, the flexible substrate 214, the connection interface 220 and/or the conductor(s) 218 can be variously configured to facilitate efficient manufacturing and operation of the ultrasound device 110.

Figure 2B:
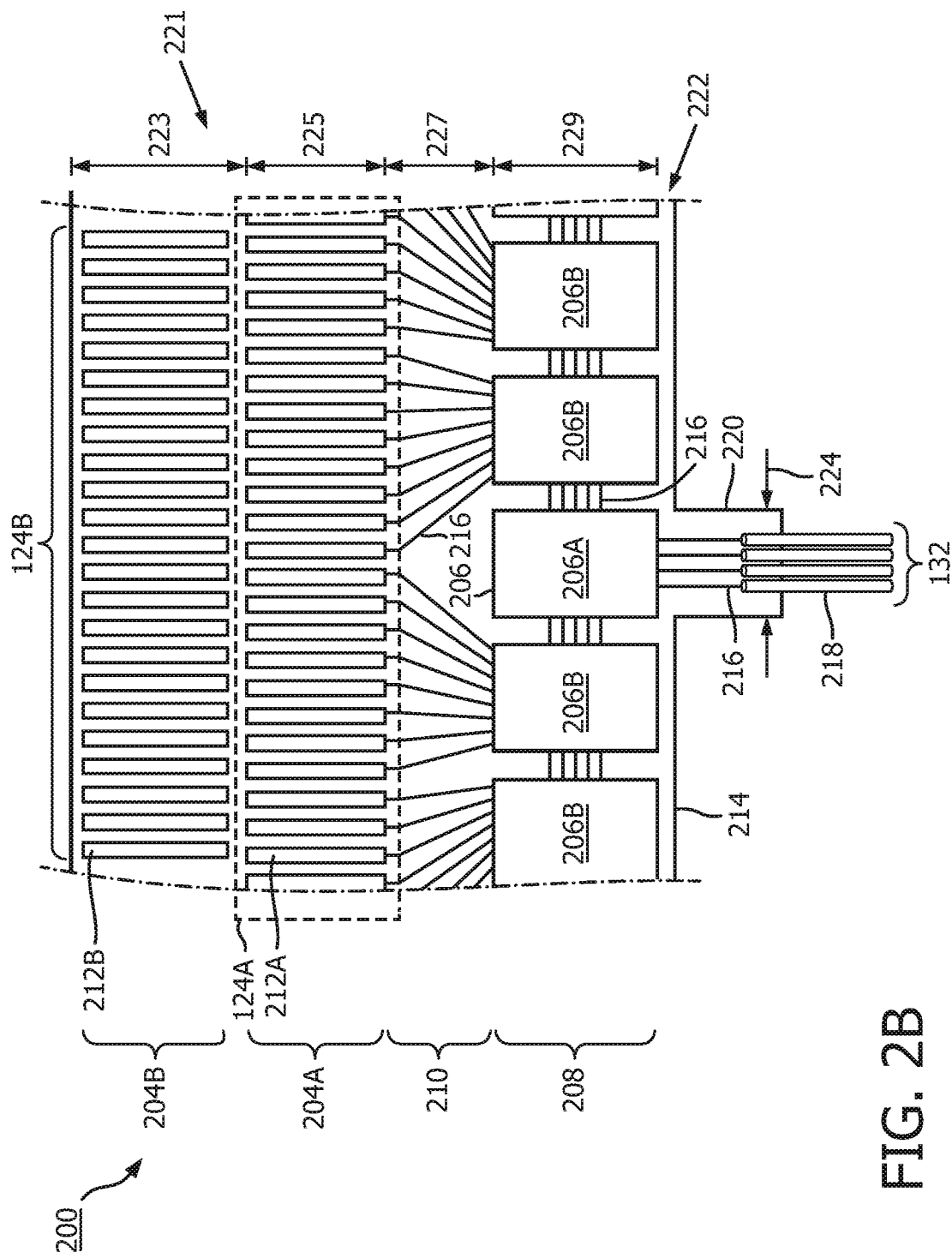
FIG. 2B is a diagrammatic top view of an transducer assembly with two ultrasound transducer arrays in a flat configuration, according to aspects of the present disclosure.
Figure 3B:
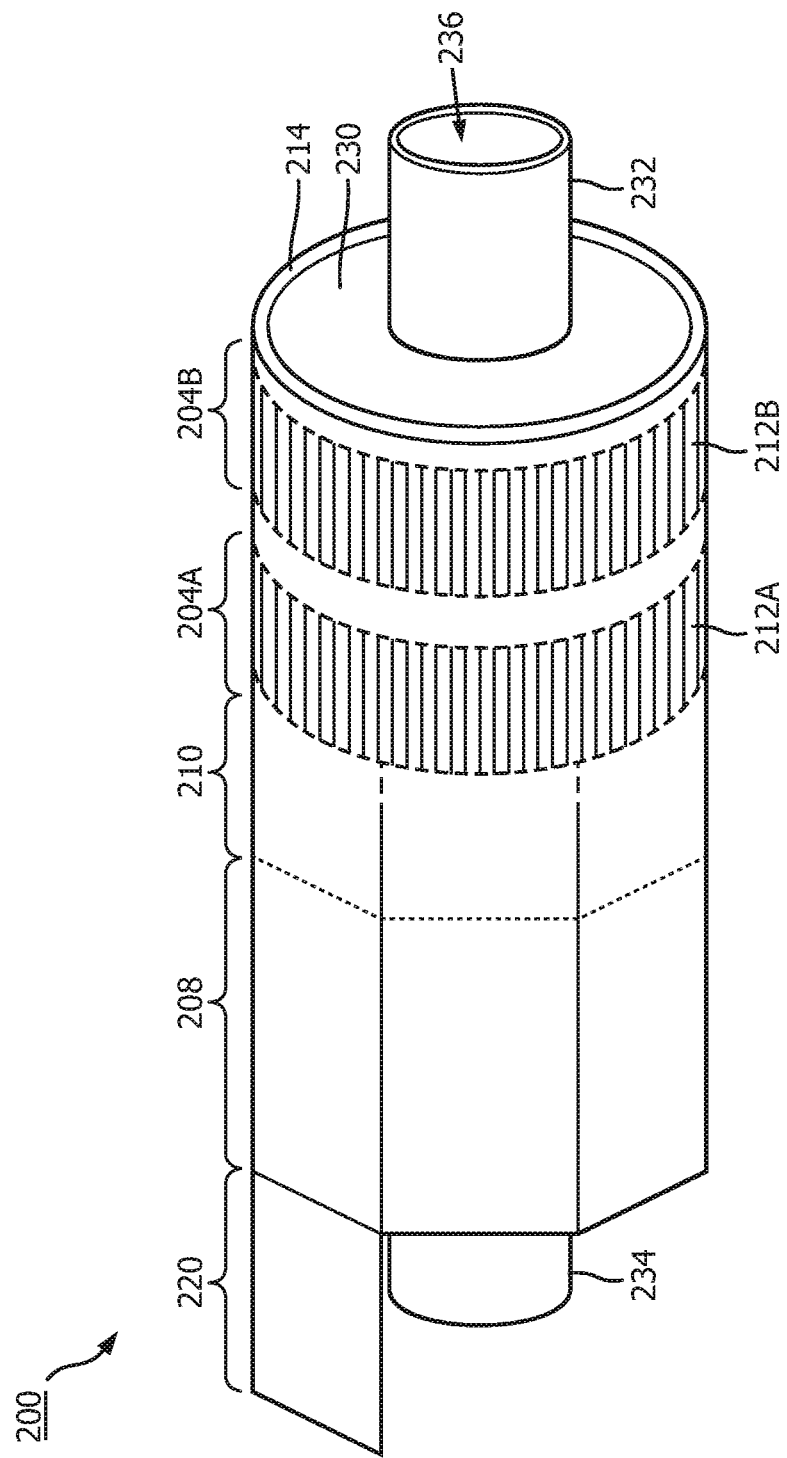
FIG. 3B is a diagrammatic perspective view of an transducer assembly with two ultrasound transducer arrays in a rolled configuration around a tubular member, according to aspects of the present disclosure.

In some instances, the transducer assembly 200 is transitioned from a flat configuration (FIGS. 2A and 2B) to a rolled or more cylindrical configuration (FIGS. 3A and 3B). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIG. 3A, the flexible substrate 214 is positioned around the tubular member 230 in the rolled configuration. FIG. 3A is a diagrammatic side view with the flexible substrate 214 in the rolled configuration around the tubular member 230, according to aspects of the present disclosure. The tubular member 230 can be referenced as a unibody in some instances. The tubular member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The tubular member 230 can have a distal section 232, a proximal section 234, and a lumen 236 extending longitudinally therethrough. The lumen 236 can be in communication with the exit port 142 and is sized and shaped to receive the guide wire 140 (FIG. 1). The tubular member 230 can be manufactured accordingly to any suitable process. For example, the tubular member 230 can be machined, such as by removing material from a blank to shape the tubular member 230, or molded, such as by an injection molding process. In some embodiments, the tubular member 230 may be integrally formed as a unitary structure, while in other embodiments the tubular member 230 may be formed of different components.

Referring now to FIG. 2B, shown therein is a top view of the transducer assembly 200 in a flat configuration according to an embodiment of the present disclosure. Different from the embodiment shown in FIG. 2A, the transducer assembly 200 illustrated in FIG. 2B includes two transducer arrays-transducer array 124A in transducer region 204A and transducer array 124B disposed in transducer region 204B. In some embodiments represented by FIG. 2B, both the transducer array 124A and the transducer array 124B are in communication with transducer control logic dies 206 (including dies 206A and 206B) formed in the control region 208 via conductive traces 216 in the transition region 210. The transducer control logic dies 206 can be referred to as control circuit 206. The transducer arrays 124A and 124B are individually controlled and activated by the control circuit 206. In some embodiments, the control circuit 206 not only can activate the whole of the transducer arrays 124A and the whole of the transducer array 124B, but also can activate a portion of the transducer arrays 124A and 124B. In some implementations, the control circuit 206 can selectively activate one of transducer arrays 124A and 124B for different applications. For instance, transducer array 124A may have a different operating frequency range from transducer 124B. By switching between transducer array 124A and 124B, the control circuit 206 can switch between applications that require different operating frequency ranges. For example, an imaging transducer array is usually operable at frequencies between 10 MHz and 70 MHz and a therapeutic transducer array is usually operable at frequencies between 1 KHz and 20 MHz. If one of the transducer arrays 124A and 124B is operable at frequencies between 10 MHz and 70 MHz and the other is operable at frequencies between 1 KHz and 20 MHz, by switching between transducer array 124A and transducer array 124B, the control circuit 206 can switch between an imaging application and a therapeutic application. In the embodiments shown in FIG. 2B, the transducer array 124A and the transducer array 124B can be referred to as the ultrasound components 120 and 130.

Referring now to FIG. 2B, shown therein is a top view of the transducer assembly 200 in a flat configuration according to an embodiment of the present disclosure. Different from the embodiment shown in FIG. 2A, the transducer assembly 200 illustrated in FIG. 2B includes two transducer arrays-transducer array 124A in transducer region 204A and transducer array 124B disposed in transducer region 204B. In some embodiments represented by FIG. 2B, both the transducer array 124A and the transducer array 124B are in communication with transducer control logic dies 206 (including dies 206A and 206B) formed in the control region 208 via conductive traces 216 in the transition region 210. The transducer control logic dies 206 can be referred to as control circuit 206. The transducer arrays 124A and 124B are individually controlled and activated by the control circuit 206. In some embodiments, the control circuit 206 not only can activate the whole of the transducer FIG. 3B illustrates a rolled configuration of the transducer assembly 200 in FIG. 2B. The transducer arrays 124A and 124B of the transducer assembly 200 are non-limiting examples of a medical sensor element and/or a medical sensor element array. The transducer control logic dies 206 is a non-limiting example of a control circuit 206. The transducer regions 204A and 204B are disposed adjacent to the distal portion 221 of the flexible substrate 214. The control region 208 is disposed adjacent to the proximal portion 222 of the flexible substrate 214. The transition region 210 is disposed between the control region 208 and the transducer region 204B. Dimensions of the transducer regions 204A and 204B, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the transducer assembly 200 is described as including a flexible substrate 214, it is understood that the transducers and/or controllers may be arranged to form the transducer assembly 200 in other configurations, including those omitting the flexible substrate 214.

The transducer array 124A may include any number and type of ultrasound transducers 212A, although for clarity only a limited number of ultrasound transducers are illustrated in FIG. 2B. The transducer array 124B may include any number and type of ultrasound transducers 212B, although for clarity only a limited number of ultrasound transducers are illustrated in FIG. 2B. In an embodiment, the transducer arrays 124A include 64 individual ultrasound transducers 212A and transducer array 124B includes 64 individual ultrasound transducers 212B. In a further embodiment, the transducer arrays 124A and 124B include 32 ultrasound transducers 212A and 212B, respectively. Other numbers are both contemplated and provided for. With respect to the types of transducers, in an embodiment, the ultrasound transducers 212A and 212B are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

In some embodiments, one of the transducer arrays 124A and 124B is configured to obtain ultrasound imaging data and the other is configured to apply an ultrasound therapy. In those embodiments, the transducer array 124B is distal to the transducer array 124A. In some implementations, the transducer array 124B is configured to obtain ultrasound imaging data and the transducer array 124A that is proximal to the transducer array 124B is configured to apply the ultrasound therapy. A person skilled in the art, upon examination of the present disclosure, would appreciate that the transducer array 124B can be configured to apply the ultrasound therapy and the transducer array 124A proximal to the transducer array 124B can be configured to obtain ultrasound imaging data.

In the embodiment where the transducer array 124B is configured to obtain ultrasound imaging data and the transducer array 124A is configured to apply an ultrasound therapy, the transducer array 124B may include various imaging control logic, which in the illustrated embodiment is divided into discrete control logic dies 206. In various examples directed to ultrasound components configured to obtain ultrasound imaging data, the imaging control logic of the ultrasound component 130 performs: decoding control signals sent by the PIM 150 across the electrical cable 132, driving one or more transducers 212B to emit an ultrasonic signal, selecting one or more transducers 212B to receive a reflected echo of the ultrasonic signal, amplifying a signal representing the received echo, and/or transmitting the signal to the PIM across the electrical cable 132. In the illustrated embodiment, an ultrasound component 130 having 64 ultrasound transducers 212B divides the control logic across nine control logic dies 206, of which five are shown in FIG. 2B. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

In some embodiments, the transducer array 124B that is configured to obtain ultrasound imaging data operates at frequencies between 10 MHz to 70 MHz. In some implementations, the transducer array 124B operates at a frequency range falling between 10 MHz and 70 MHz. For ease of reference, this frequency range is referred to as diagnostic frequency range. In some instances, the diagnostic frequency range includes a median.

In the embodiment where the transducer array 124A is configured to apply an ultrasound therapy, the transducer array 124B may include various therapy control logic, which in the illustrated embodiment is divided into discrete control logic dies 206. In various examples directed to transducer assemblies configured to apply an ultrasound therapy, the therapy control logic of the transducer assembly 200 performs: decoding control signals sent by the PIM 150 across the electrical cable 132, and driving one or more transducers 212A to emit an ultrasonic signal. In the illustrated embodiment, the transducer array 124A having 64 ultrasound transducers 212A divides the control logic across nine control logic dies 206, of which five are shown in FIG. 2B. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

In some embodiments, the transducer array 124A configured to apply an ultrasound therapy operates at frequencies between 1 KHz to 20 MHz. In some implementations, the transducer array 124A operates at a frequency range falling between 1 KHz and 20 MHz, in some cases between 1 KHz and 5 MHz. For ease of reference, this frequency range is referred to as therapeutic frequency range. In some instances, the therapeutic frequency range includes a median. The median of the imaging frequency range is different from the median of the therapeutic frequency range. In some instances, the imaging frequency range overlaps with the therapeutic frequency range. In some other instances, the imaging frequency range does not overlap with the therapeutic frequency range.

The control logic dies are not necessarily homogenous. In some embodiments shown in FIG. 2B, a single controller is designated a master control logic die 206A and contains the communication interface for the electrical cable 132. Accordingly, the master control circuit may include control logic that decodes control signals received over the electrical cable 132, transmits control responses over the electrical cable 132, amplifies echo signals, and/or transmits the echo signals over the electrical cable 132. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEF-LON® (registered trademark of E.I. du Pont). In the flat configuration illustrated in FIG. 2B, the flexible substrate 214 has a generally rectangular shape. As shown and described herein, the flexible substrate 214 is configured to be wrapped around a tubular member 230 (FIG. 3B) to form a cylindrical toroid in some instances. Therefore, the thickness of the film layer of the flexible substrate 214 is generally related to the degree of curvature in the final assembled transducer arrays 124A and 124B. In some embodiments, the film layer is between 5 μm and 100 μm, with some particular embodiments being between 12.7 μm and 25.1 μm.

To electrically interconnect the control logic dies 206 and the transducers 212A and 212B, in an embodiment, the flexible substrate 214 further includes conductive traces 216 formed on the film layer that carry signals between the control logic dies 206 and the transducers 212A and 212B. In particular, the conductive traces 216 providing communication between the control logic dies 206 and the transducers 212A and 212B extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of electrical cable 132 when the conductors 218 of the electrical cable 132 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 10-50 μm. For example, in an embodiment, 20 μm conductive traces 216 are separated by 20 μm of space. The width of a conductive trace 216 on the flexible substrate 214 may be further determined by the width of the conductor 218 to be coupled to the trace/pad.

The flexible substrate 214 can include a connection interface 220 in some embodiments. The connection interface 220 can be a location of the flexible substrate 214 where the conductors 218 of the electrical cable 132 are coupled to the flexible substrate 214. For example, the bare conductors of the electrical cable 132 are electrically coupled to the flexible substrate 214 at the connection interface 220. The connection interface 220 can be a tab extending from the main body of flexible substrate 214. In that regard, the main body of the flexible substrate 214 can refer collectively to the transducer region 204, controller region 208, and the transition region 210. In the illustrated embodiment, the connection interface 220 extends from the proximal portion 222 of the flexible substrate 214. In other embodiments, the connection interface 220 is positioned at other parts of the flexible substrate 214, such as the distal portion 221, or the flexible substrate 214 omits the connection interface 220. A value of a dimension of the tab or connection interface 220, such as a width 224, can be less than the value of a dimension of the main body of the flexible substrate 214, such as a width 226. In some embodiments, the substrate forming the connection interface 220 is made of the same material(s) and/or is similarly flexible as the flexible substrate 214. In other embodiments, the connection interface 220 is made of different materials and/or is comparatively more rigid than the flexible substrate 214. For example, the connection interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the tubular member 230, the flexible substrate 214, the connection interface 220 and/or the conductor(s) 218 can be variously configured to facilitate efficient manufacturing and operation of the ultrasound device 110.

In some instances, the transducer assembly 200 is transitioned from a flat configuration (FIGS. 2A and 2B) to a rolled or more cylindrical configuration (FIGS. 3A and 3B). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIG. 3B, the flexible substrate 214 is positioned around the tubular member 230 in the rolled configuration. FIG. 3B is a diagrammatic side view with the flexible substrate 214 in the rolled configuration around the tubular member 230, according to aspects of the present disclosure. The tubular member 230 can be referenced as a unibody in some instances. The tubular member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The tubular member 230 can have a distal section 232, a proximal section 234, and a lumen 236 extending longitudinally therethrough. The lumen 236 can be in communication with the exit port 142 and is sized and shaped to receive the guide wire 140 (FIG. 1). The tubular member 230 can be manufactured accordingly to any suitable process. For example, the tubular member 230 can be machined, such as by removing material from a blank to shape the tubular member 230, or molded, such as by an injection molding process. In some embodiments, the tubular member 230 may be integrally formed as a unitary structure, while in other embodiments the tubular member 230 may be formed of different components.

FIG. 3B illustrates a rolled configuration of the flexible substrate 214 in FIG. 2B. The transducer arrays 124A and 124B are a non-limiting example of a medical sensor element and/or a medical sensor element array. The transducer control logic dies 206 is a non-limiting example of a control circuit 206. The transducer region 204 is disposed adjacent a distal portion 221 of the flexible substrate 214. The control region 208 is disposed adjacent the proximal portion 222 of the flexible substrate 214. The transition region 210 is disposed between the control region 208 and the transducer region 204. Dimensions of the transducer region 204, the control region 208, and the transition region 210 (e.g., lengths 223, 225, 227, 229) can vary in different embodiments. In some embodiments, the lengths 223, 225, 227, 229 can be substantially similar or a length 227 of the transition region 210 can be greater than lengths 223, 225, 229 of the transducer region and controller region, respectively. While the transducer assembly 200 is described as including the flexible substrate 214, it is understood that the transducers and/or controllers may be arranged to form the transducer assembly in other configurations, including those omitting flexible substrate 214.

Figure 4:
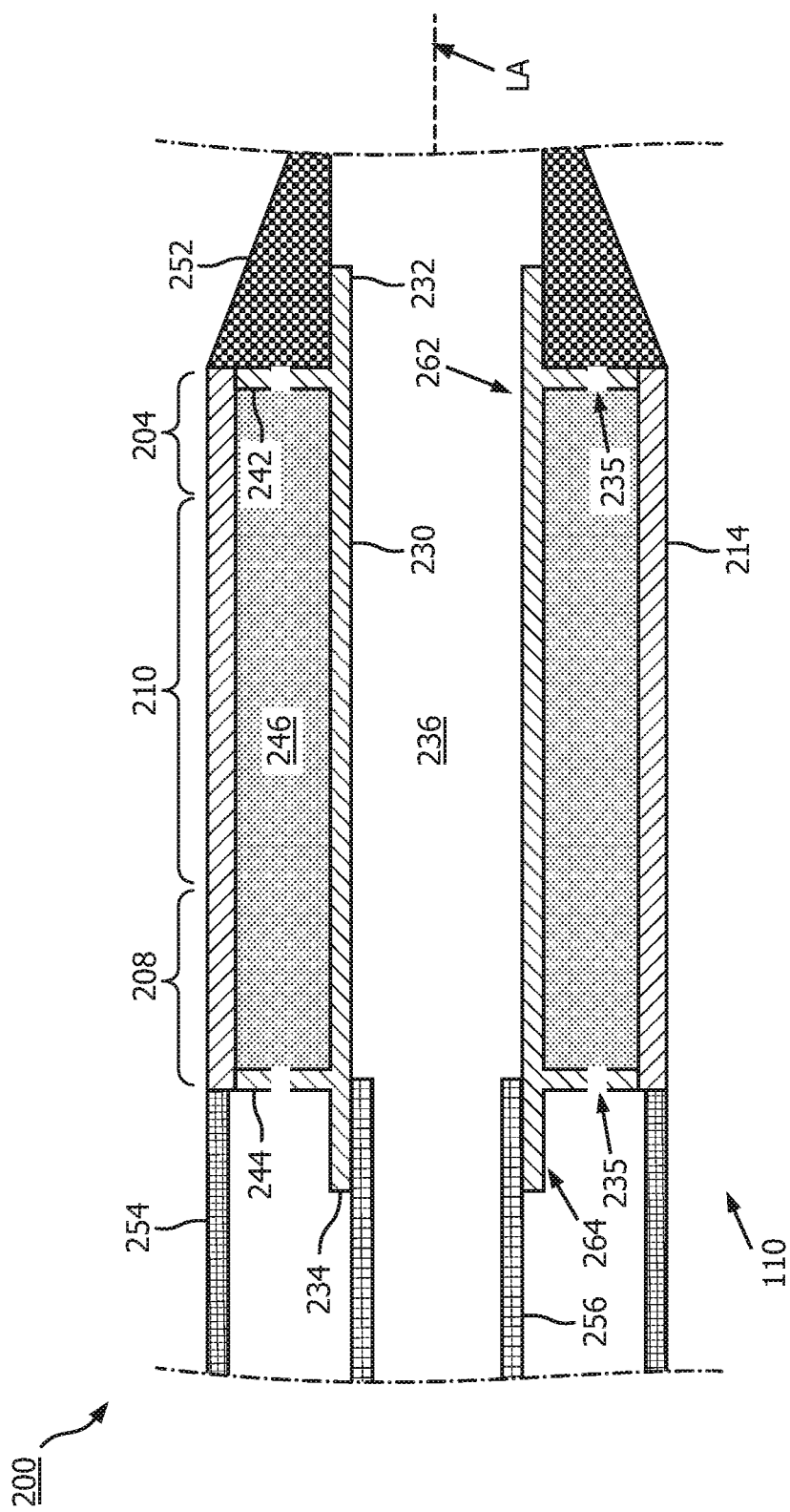
FIG. 4 is a diagrammatic cross-sectional side view of an transducer assembly with an ultrasound transducer array, according to aspects of the present disclosure.

Referring now to FIG. 4, shown there is a diagrammatic cross-sectional side view of a distal portion of the ultrasound device 110, including the flexible substrate 214 and the tubular member 230, according to aspects of the present disclosure. The tubular member 230 can be referenced as a unibody in some instances. The tubular member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The tubular member 230 can be ferrule having a distal portion 262 and a proximal portion 264. The tubular member 230 can define a lumen 236 extending along the longitudinal axis LA. The lumen 236 is in communication with the exit port 142 and is sized and shaped to receive the guide wire 140 (FIG. 1). The tubular member 230 can be manufactured accordingly to any suitable process. For example, the tubular member 230 can be machined, such as by removing material from a blank to shape the tubular member 230, or molded, such as by an injection molding process. In some embodiments, the tubular member 230 may be integrally formed as a unitary structure, while in other embodiments the tubular member 230 may be formed of different components, such as a ferrule and stands 242, 244, that are fixedly coupled to one another.

Stands 242, 244 that extend vertically are provided at the distal and proximal portions 262, 264, respectively, of the tubular member 230. The stands 242, 244 elevate and support the distal and proximal portions of the flexible substrate 214. In that regard, portions of the flexible substrate 214, such as the transducer portion 204 (or transducer region 204), can be spaced from a central body portion of the tubular member 230 extending between the stands 242, 244. Although not shown in FIG. 4, in cases where there are transducer regions 204A and 204B, the transducer regions 204A and 204B are adjacent to one another and are distal to the transition region 210. The stands 242, 244 can have the same outer diameter or different outer diameters. For example, the distal stand 242 can have a larger or smaller outer diameter than the proximal stand 244. To improve acoustic performance, any cavities between the flexible substrate 214 and the surface of the tubular member 230 are filled with a backing material 246. The liquid backing material 246 can be introduced between the flexible substrate 214 and the tubular member 230 via passageways 235 in the stands 242, 244. In some embodiments, suction can be applied via the passageways 235 of one of the stands 242, 244, while the liquid backing material 246 is fed between the flexible substrate 214 and the tubular member 230 via the passageways 235 of the other of the stands 242, 244. The backing material can be cured to allow it to solidify and set. In various embodiments, the tubular member 230 includes more than two stands 242, 244, only one of the stands 242, 244, or neither of the stands. In that regard the tubular member 230 can have an increased diameter distal portion 262 and/or increased diameter proximal portion 264 that is sized and shaped to elevate and support the distal and/or proximal portions of the flexible substrate 214.

The tubular member 230 can be substantially cylindrical in some embodiments. Other shapes of the tubular member 230 are also contemplated including geometrical, non-geometrical, symmetrical, non-symmetrical, cross-sectional profiles. Different portions the tubular member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the tubular member 230 (e.g., the diameter of the lumen 236) can correspondingly increase or decrease as the outer diameter changes. In other embodiments, the inner diameter of the tubular member 230 remains the same despite variations in the outer diameter.

A proximal inner member 256 and a proximal outer member 254 are coupled to the proximal portion 264 of the tubular member 230. The proximal inner member 256 and/or the proximal outer member 254 can be part of the flexible elongate member 116 that extend from proximal portion of the ultrasound device 110, such as the interface 156 (FIG. 1), to the ultrasound component 120/130. For example, the proximal inner member 256 can be received within a proximal flange 234. The proximal outer member 254 abuts and is in contact with the flexible substrate 214. A distal member 252 is coupled to the distal portion 262 of the tubular member 230. The distal member 252 can be a flexible component that defines a distal most portion of the ultrasound device 110. For example, the distal member 252 is positioned around the distal flange 232. The distal member 252 can abut and be in contact with the flexible substrate 214 and the stand 242. The distal member 252 can be the distal-most component of the ultrasound device 110.

One or more adhesives can be disposed between various components at the distal portion of the ultrasound device 110. For example, one or more of the flexible substrate 214, the tubular member 230, the distal member 252, the proximal inner member 256, and/or the proximal outer member 254 can be coupled to one another via an adhesive.

Figure 5:
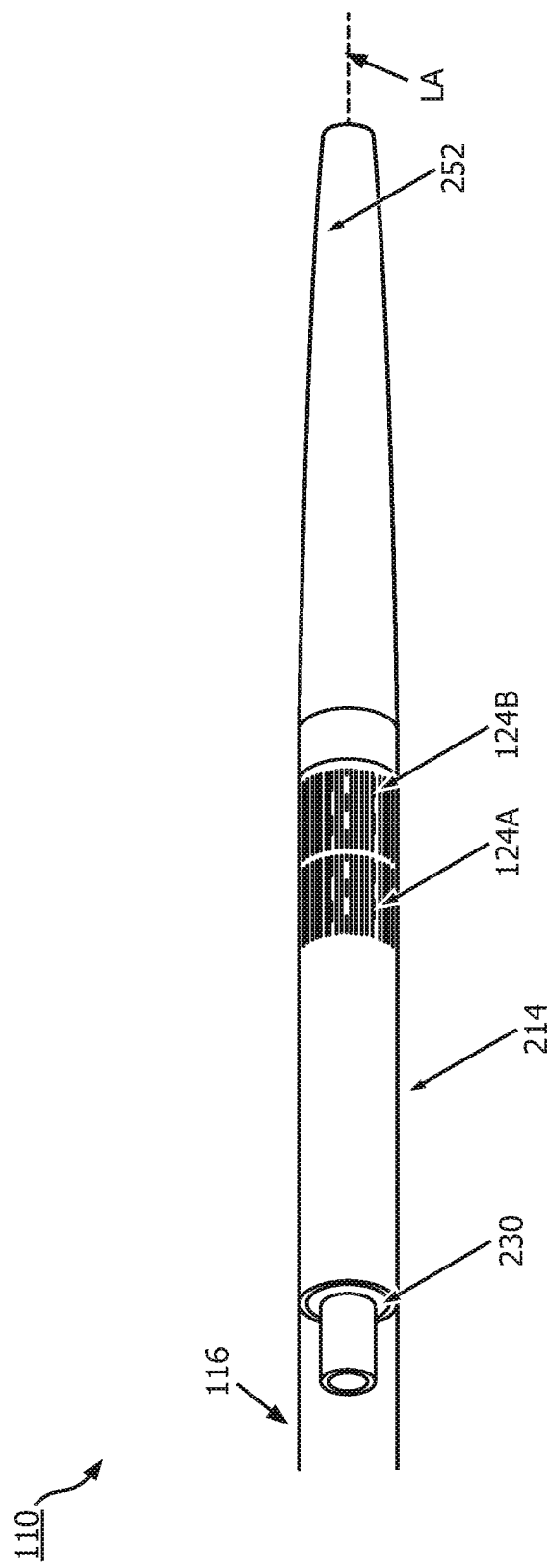
FIG. 5 is a diagrammatic perspective view of a distal portion of an ultrasound device, according to aspects of the present disclosure.
Figure 6:
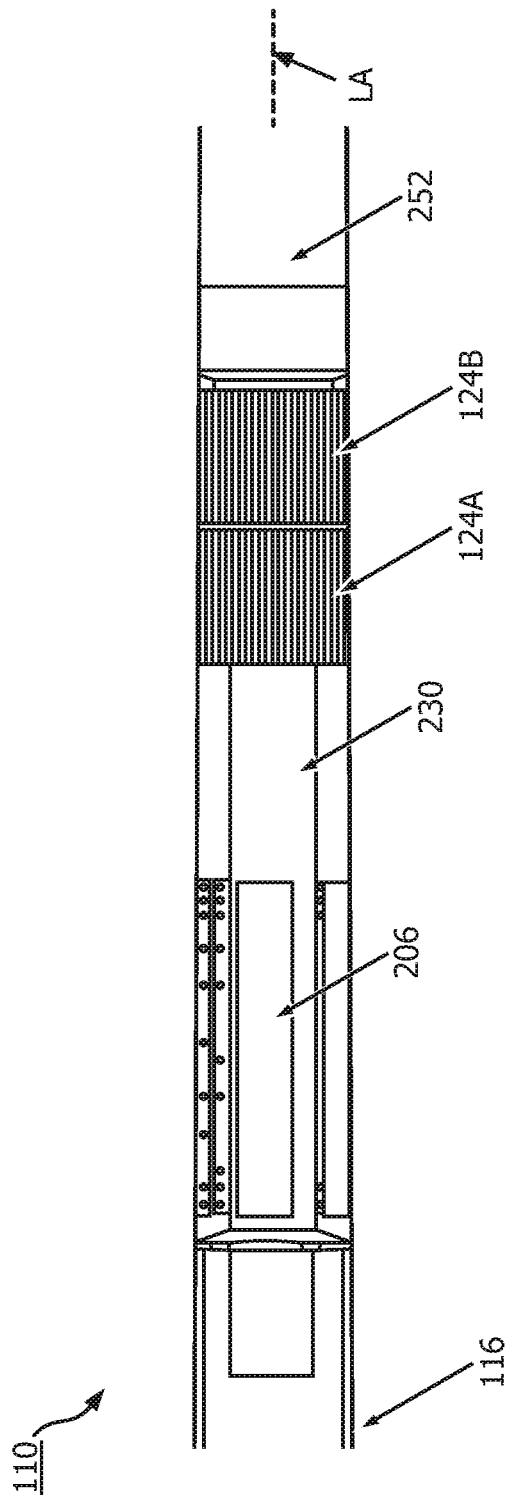
FIG. 6 is a diagrammatic side view of an transducer assembly in a distal portion of an ultrasound device, according to aspects of the present disclosure.

Reference is now made to FIG. 5. Shown there is a diagrammatic cross-sectional perspective view of a distal portion of the ultrasound device 110, including the flexible substrate 214 and the tubular member 230, according to aspects of the present disclosure. FIG. 5 is one of the implementations that incorporate the ultrasound components 120 and 130 shown in FIG. 3B. In some embodiments, the ultrasound component 120 is operable at frequencies between 1 KHz and 20 MHz to obtain ultrasound imaging data and the ultrasound component 130 is operable at frequencies between 10 MHz and 70 MHz to apply an ultrasound therapy. In some instances, the ultrasound component 120 is operable at a first frequency range falling between 1 KHz and 20 MHz and the ultrasound component is operable at a second frequency range falling between 10 MHz and 70 MHz. In some other implementations, the ultrasound component 120 is operable at a first frequency range falling between 1 KHz and 5 MHz. The median of the first frequency range is different from the median of the second frequency range. In some instances, the first frequency range and the second frequency range do not overlap. As described above with reference to FIG. 3B, the ultrasound components 120 and 130 include transducer arrays 124A and 124B. As shown in FIG. 6, which is an enlarged view of the distal portion of the ultrasound device 110 shown in FIG. 5, the transducer arrays 124A and 124B are mounted on the flexible substrate 214 and the flexible substrate 214 is wrapped around the tubular member 230. As the tubular member 230 is coaxial with the longitudinal axis LA, transducer arrays 124A and 124B can be said to be circumferentially positioned around the longitudinal axis LA of the flexible elongate member 116. In some embodiments, the transducer arrays 124A and 124B of ultrasound components 120 and 130 are individually controlled and activated by the control circuit 206 in FIG. 6. In some implementations, the control circuit 206 can selectively activate one of transducer arrays 124A and 124B for different applications. That is, the control circuit 206 can switch between transducer arrays 124A and 124B to switch between a mode for obtaining ultrasound imaging data and another mode for applying an ultrasound therapy.

Figure 7:
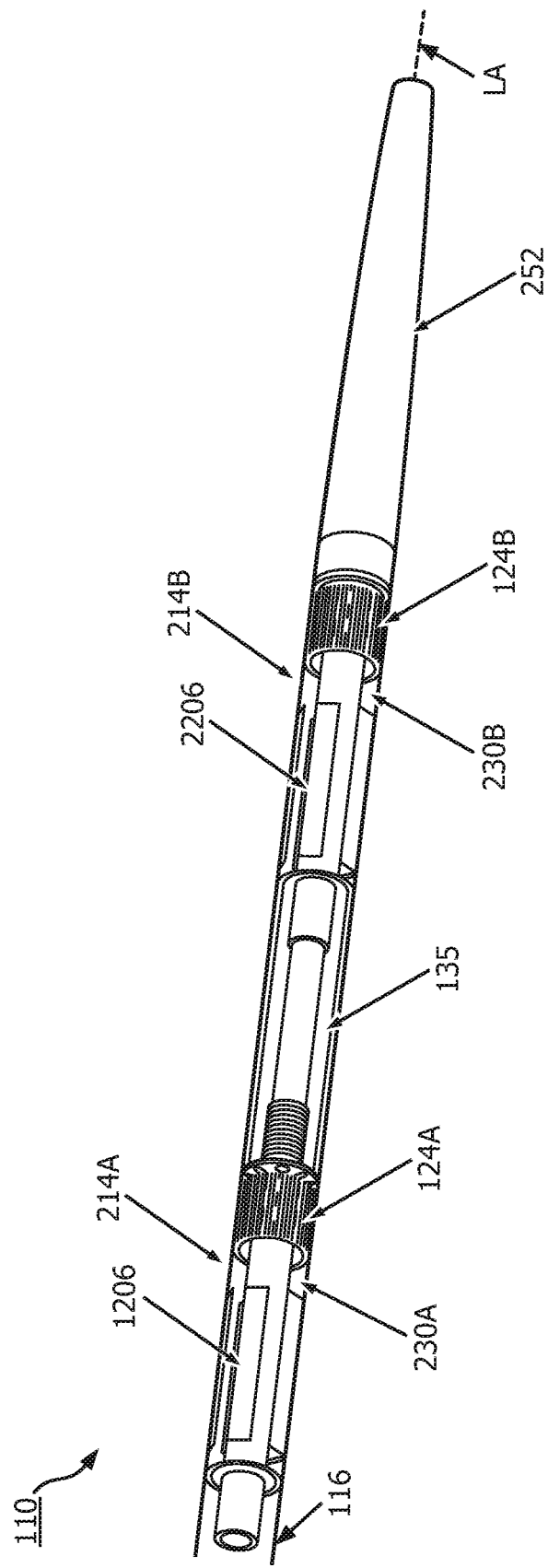
FIG. 7 is a diagrammatic perspective view of a distal portion of an ultrasound device, according to aspects of the present disclosure.

Referring now to FIG. 7, shown therein is a diagrammatic perspective view of the distal portion of the ultrasound device 110 according to another embodiment of the present disclosure. In this embodiment, ultrasound components 120 and 130 do not share the same tubular member and control circuit. In this regard, the ultrasound component 120, along with the transducer array 124A, is mounted on a first flexible substrate 214A. The first flexible substrate 214A is wrapped around a first tubular member 230A. Also mounted on the first flexible substrate 214A is a first control circuit 1206. Although not shown in FIG. 7, similar to control circuit 206, the first control circuit 1206 may include multiple master controller and multiple slave controller. In some embodiments, the first control circuit 1206 activates and controls only the ultrasound component 120. That is, the first control circuit 1206 is a control circuit dedicated to ultrasound component 120. The ultrasound component 130 and its transducer array 124B is mounted a second flexible substrate 214B. The second flexible substrate 214B is wrapped around a second tubular member 230B. Also mounted on the second flexible substrate 214B is a second control circuit 2206. Although not shown in FIG. 7, similar to control circuit 206, the second control circuit 2206 may include multiple master controller and multiple slave controller. In some embodiments, the second control circuit 2206 activates and controls only the ultrasound component 130. That is, the second control circuit 2206 is a control circuit dedicated to ultrasound component 130. The first tubular member 230A and the second tubular member 230B are coupled together by a flexible joint 135. In some implementations, the flexible joint 135 can be a spring coil or an elastic tubular member.

The embodiment represented by FIG. 7 presents several benefits. First, because the ultrasound components 120 and 130 do not share a common control circuit, the architecture of the control circuit can be simplified and switching between the imaging and therapeutic mode involves only one of the control circuits. In some embodiments, electrical signals supplied to the first control circuit 1206 and the second control circuit 2206 can be completely separate, allowing use of separate sets of electrical wires. Second, the flexible joint 135 between the first and second tubular member 230A and 230B allows the distal portion of the resultant ultrasound device 110 to be more flexible, thus more steerable. As discussed above with reference to FIGS. 3A and 3B, tubular members such as the first and second tubular members 230A and 230B are oftentimes made of rigid materials, such as stainless steel. By having two separate and shorter ultrasound assemblies connected by a flexible joint, the distal portion of the ultrasound device 110 is allowed to have a shorter stiff section. In most cases, having a shorter stiff section means that the distal portion of the ultrasound device 110 can be inserted to more tortuous body lumens or vessels with tighter turns. This "shorter stiff section" feature also allows smoother insertion of the ultrasound device 110 to the desired location. Third, the greater distance separating the ultrasound component 120 and the ultrasound component 130 may result in reduced interference between these two components during simultaneous operation. That is, by separating ultrasound components 120 and 130.

Referring back to FIG. 1, the ultrasound device 110 includes a treating component 145 in some embodiments. For example, the treatment component 145 can include a balloon, a stent, a needle, an ablation electrode, mechanical cutting component, a rotational cutting device, an aspiration device, and/or other suitable devices. The treatment component 145 can be a targeted drug delivery device, a drug coated balloon, a drug coated stent, and/or other suitable device configured to deliver a pharmacological agent to the anatomy 102, such as the occlusion 106.

Figure 8A:
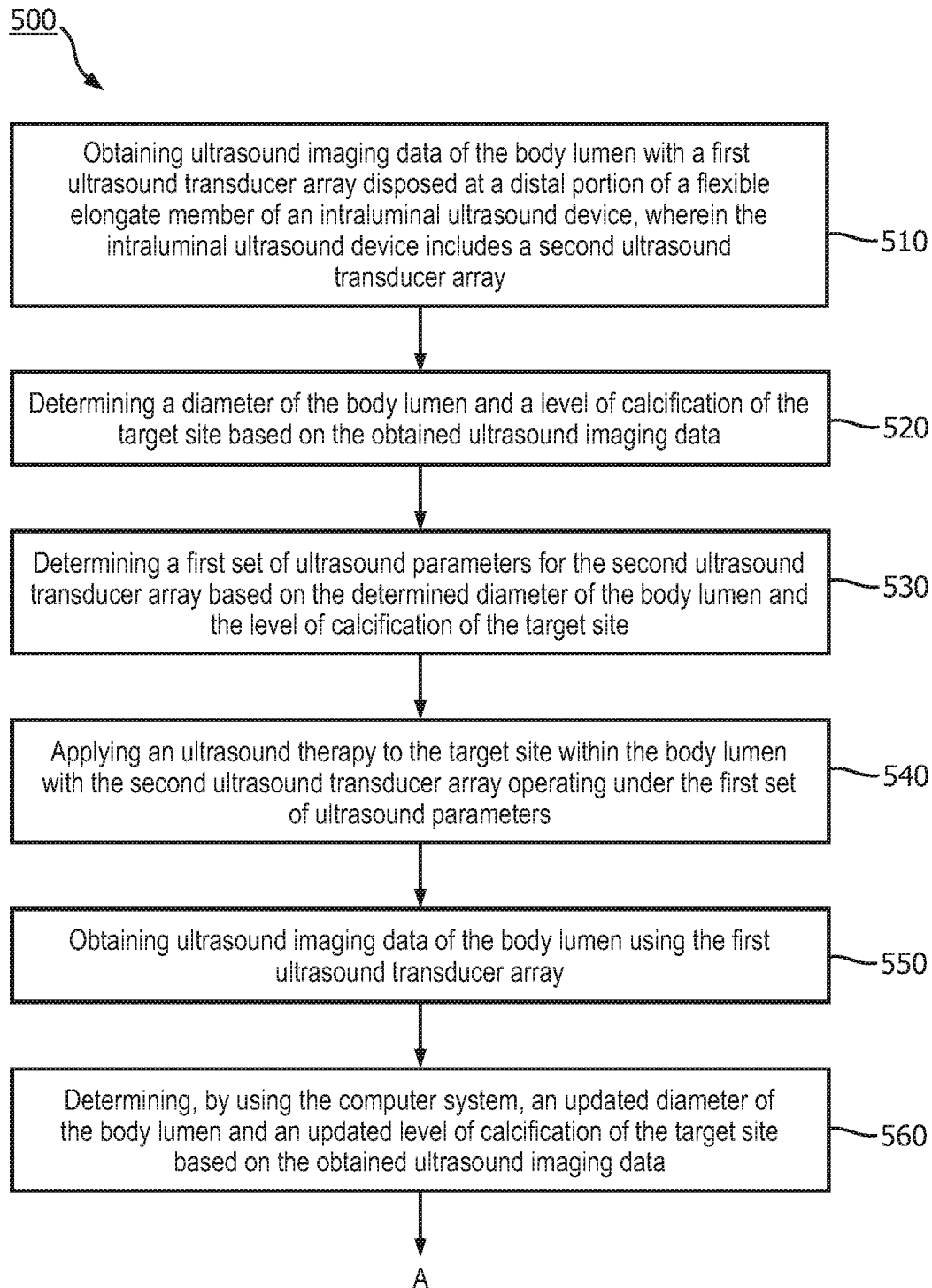
FIGS. 8A and 8B are a flow diagram of a method of treating a target site using an ultrasound device according to aspects of the present disclosure.
Figure 8B:
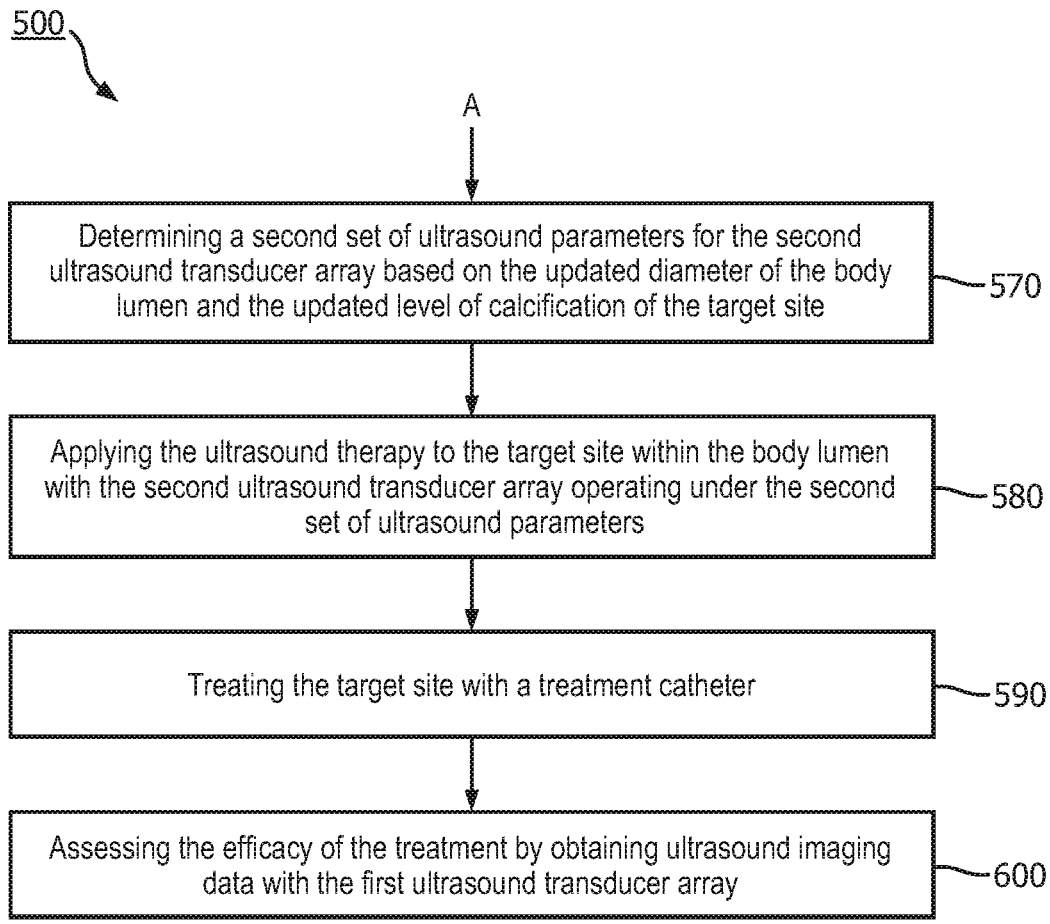

FIGS. 8A and 8B show a flow diagram of a method 500 of treating a target site, such as the occlusion 106 in FIG. 1 within a body lumen of a patient, according to aspects of the present disclosure. The method 500 includes operations 510, 520, 530, 540, 550, 560, 570, 580, 590, and 600. For illustration purposes, the operations of method 500 will be described with reference to FIGS. 1 and 2B. At operation 510, ultrasound imaging data of the body lumen 104 is obtained with use of a first ultrasound transducer array (transducer array 124B of ultrasound component 130) disposed at the distal portion 114 of the flexible elongate member 116 of the intraluminal ultrasound device 110. The first ultrasound transducer array 124B is circumferentially positioned around the longitudinal axis LA of the flexible elongate member 116 and is configured to obtain ultrasound imaging data of the body lumen 104. The intraluminal ultrasound device 110 includes a second ultrasound transducer array (transducer array 124A of ultrasound component 120) operable to apply an ultrasound therapy with the body lumen 104. The second ultrasound transducer array 124A is disposed at the distal portion 114 of the flexible elongate member 116 and is circumferentially positioned around the longitudinal axis LA of the flexible elongate member 116.

At operation 520, a diameter of the body lumen 104 and a level of calcification of the target site, such as the occlusion 106 in FIG. 1, is determined based on the ultrasound imaging data obtained at operation 510. In general, a target site, such as occlusion 106 in FIG. 6, tends to reflect more ultrasound energy when it has a higher level of calcification. That is, by measuring the intensity of the ultrasound signal associated with ultrasound echoes reflected from the target site, the level of calcification of the target site can be determined. For example, virtual histology (VH) methods and algorithms can be used to determine the boundary of the blood vessel wall defining the body lumen 104 and the density of a target site, such as the occlusion 106. Detecting and characterizing plaque using IVUS with VH are described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NONINVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

At operation 530, a first set of ultrasound parameters for the second ultrasound transducer array 124A is determined based on the diameter of the body lumen 104 and the level of calcification of the target site determined at operation 520. Depending on the diameter of the body lumen 104 where the target site is positioned and the level of calcification of the target site, effective treatment of the target site requires an ultrasound therapy with ultrasound pulses with different frequencies, different pulse amplitudes, and different pulse lengths. Once the diameter of the body lumen 104 and the level of calcification of the target site are determined at operation 520, an ultrasound processing system 160 in communication of the ultrasound device 110 can determine a first set of ultrasound parameters that are optimal for effective treatment of the target site. After the ultrasound processing system 160 determines the first set of ultrasound parameters, the ultrasound processing system 160 can adjust the electrical signals it transmits to the control circuit 206 such that the second ultrasound transducer array 124A operates under the first set of ultrasound parameters.

At operation 540, an ultrasound therapy is applied to the target site within the body lumen 104 with the second ultrasound transducer array 124A operating under the first set of ultrasound parameters.

At operation 550, ultrasound imaging data of the body lumen 104 is obtained using the first ultrasound transducer array 124B. To assess the efficacy of the ultrasound therapy applied at operation 540, ultrasound imaging data of the lumen 104 is obtained again by the first ultrasound transducer array 124B.

At operation 560, an updated diameter of the body lumen 104 and an updated level of calcification of the target site are determined by the ultrasound processing system 160, based on the ultrasound imaging data obtained at operation 550. As an ultrasound therapy has been applied to the target site, the diameter of the body lumen 104 and the level of calcification of the target site may have reduced. To determine the updated diameter of the body lumen 104 and the updated level of calcification of the target, ultrasound imaging data of the lumen 104 is obtained again with use of the first ultrasound transducer array 124B.

At operation 570, a second set of ultrasound parameters for the second ultrasound transducer array 124A is determined based on the updated diameter of the body lumen 104 and the updated level of calcification of the target site. Based on parameters stored in the ultrasound processing system 160, the ultrasound processing system 160 can determine whether further ultrasound therapies are required. If no further ultrasound therapies are required, method 500 would skip operation 590 and proceed directly to operation 600. If further ultrasound therapies are required, the ultrasound processing system 160 generate a second set of ultrasound parameters that are optimal for effective treatment of the target site.

At operation 580, the ultrasound therapy is applied to the target site within the body lumen 104 with the second ultrasound transducer array 124A operating under the second set of ultrasound parameters.

At operation 590, the target site is treated with the treatment component 145. Finally, at operation 600, to assess the efficacy of the treatment by the treatment component 145, ultrasound imaging data of the body lumen 104 is obtained using the first ultrasound transducer array 124B.

The systems, devices, and methods of the present disclosure can include features described in U.S. Provisional App. No. 62/545,944, filed on an even date herewith, U.S. Provisional App. No. 62/545,954, filed on an even date herewith, U.S. Provisional App. No. 62/545,927, filed on an even date herewith, and/or U.S. Provisional App. No. 62/545,888, filed on an even date herewith, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound device, comprising:
a flexible elongate member configured to be positioned within a body lumen of a patient, the flexible elongate member including a distal portion and a longitudinal axis, the flexible elongate member comprising a first tubular member and a second tubular member connected by a flexible joint;
a first ultrasound transducer array disposed distally from the flexible joint, the first ultrasound array being circumferentially positioned around the longitudinal axis of the flexible elongate member, wherein the first ultrasound transducer array is configured to obtain ultrasound imaging data of the body lumen; and
a second ultrasound transducer array disposed proximally from the flexible joint and adjacent a distal member of the distal portion of the flexible elongate member, the second ultrasound array being circumferentially positioned around the longitudinal axis of the flexible elongate member, wherein the second ultrasound transducer array is configured to apply an ultrasound therapy within the body lumen.

2. The intraluminal ultrasound device of claim 1 further comprising a plurality of control logic dies disposed on the flexible elongate member and coupled by a plurality of signal lines to the first and second ultrasound transducer arrays.

3. The intraluminal ultrasound device of claim 2, wherein the control logic dies are further configured to multiplex signals transmitted on the plurality of signal lines to activate selected portions of the first and second ultrasound transducer arrays for generating ultrasonic pulses and for receiving ultrasonic echoes.

4. The intraluminal ultrasound device of claim 2 wherein the control logic dies are configured to selectively activate a whole or part of the first ultrasound transducer array and the second ultrasound transducer array.

5. The intraluminal ultrasound device of claim 1 wherein the flexible joint comprises a spring coil.

6. The intraluminal ultrasound device of claim 1 wherein the flexible joint comprises an elastic tubular member.

7. A method for treating a target site within a body lumen of a patient comprising:
  positioning a flexible elongate member of an intraluminal ultrasound device within the body lumen of the patient, the flexible elongate member including a first ultrasound transducer array and a second transducer array;
  obtaining ultrasound imaging data of the body lumen with the first ultrasound transducer array of the intraluminal ultrasound device; and
  applying ultrasound therapy to the target site within the body lumen with the second ultrasound transducer array;
  wherein the flexible elongate member comprises a distal portion and has a longitudinal axis, the flexible elongate member comprising a first tubular member and a second tubular member connected by a flexible joint, the first ultrasound transducer array being disposed distally from the flexible joint and the second ultrasound transducer array disposed proximally from the flexible joint.

8. The method of claim 7, wherein the intraluminal ultrasound device is in communication with an ultrasound processing system, the method further comprising:
  after obtaining ultrasound imaging data of the body lumen, determining by the ultrasound processing system, a diameter of the body lumen and a level of calcification of the target site based on the obtained ultrasound imaging data; and
  determining a first set of ultrasound parameters for the second ultrasound transducer array based on the determined diameter of the body lumen and the level of calcification of the target site.

9. The method of claim 8, wherein the second ultrasound transducer array operates under the first set of ultrasound parameters when applying the ultrasound therapy to the target site with the second ultrasound transducer array.

10. The method of claim 9, further comprising:
  after the applying of the ultrasound therapy to the target site, obtaining second ultrasound imaging data of the body lumen using the first ultrasound transducer array;
  determining, by using the ultrasound processing system, an updated diameter of the body lumen and an updated level of calcification of the target site based on the second ultrasound imaging data;
  determining a second set of ultrasound parameters for the second ultrasound transducer array based on the updated diameter of the body lumen and the updated level of calcification of the target site; and
  applying the ultrasound therapy to the target site within the body lumen with the second ultrasound transducer array operating under the second set of ultrasound parameters.

11. The method of claim 10, wherein the first and second sets of ultrasound parameters each comprise a frequency, a pulse amplitude, and a pulse length.

12. The method of claim 7 wherein:
  the intraluminal ultrasound device comprises a flexible substrate wrapped around the distal portion of the flexible elongate member and circumferentially positioned around the longitudinal axis of the flexible elongate member;
  the first and second ultrasound transducer arrays are both mounted on the flexible substrate so that the first and second ultrasound transducer arrays are circumferentially positioned around the longitudinal axis of the flexible elongate member; and
  the intraluminal ultrasound device further comprises a plurality of control logic dies disposed on the flexible substrate and coupled by a plurality of signal lines to the first and second ultrasound transducer arrays, the plurality of control logic dies comprising a master control logic die and at least one non-master control logic die.

* * * * *